United States Patent [19]

Isogai et al.

[11] Patent Number: 5,563,667
[45] Date of Patent: Oct. 8, 1996

[54] OPTHALMIC APPARATUS HAVING LOWERED CONSUMPTION OF ELECTRIC POWER

[75] Inventors: Naoki Isogai, Nishio; Yoshiaki Mimura, Gamagori; Masanao Fujieda, Toyohashi, all of Japan

[73] Assignee: Nidek Co., Ltd., Japan

[21] Appl. No.: 330,799

[22] Filed: Oct. 28, 1994

[30] Foreign Application Priority Data

Oct. 29, 1993 [JP] Japan .................................. 5-294408

[51] Int. Cl.⁶ ........................................................ A61B 3/14
[52] U.S. Cl. ............................................ 351/208; 351/221
[58] Field of Search ..................................... 351/208, 221, 351/209, 247, 205, 212

[56] References Cited

U.S. PATENT DOCUMENTS 4,863,259   9/1989   Schneider et al. .................... 351/210

FOREIGN PATENT DOCUMENTS

0364154A1   4/1990   European Pat. Off. ............... 351/208
1-19896     4/1989   Japan .

Primary Examiner—William L. Sikes
Assistant Examiner—James A. Dudek
Attorney, Agent, or Firm—Finnegan, Henderson, Farabow, Garrett & Dunner

[57] ABSTRACT

An ophthalmic apparatus for measuring an eye of an examinee, includes a device for detecting whether the eye is located within a predetermined area with respect to the apparatus, an interval time producing device for producing a prescribed interval time, a power supply device for supplying power intermittently to the detecting device in accordance with signals for the interval time producing device, and power supply signal generating device for generating a signal to supply a power required by the ophthalmic apparatus when the detecting device judges that the eye exists within the predetermined area.

15 Claims, 7 Drawing Sheets

OPTHALMIC APPARATUS HAVING LOWERED CONSUMPTION OF ELECTRIC POWER

BACKGROUND OF THE INVENTION

1. Field of the Invention

The present invention relates to an ophthalmic apparatus, and more particularly to an ophthalmic apparatus usable as apparatus of battery type and of hand-held type.

2. Description of Related Art

In general, the on-off control of electric power to cornea shape measuring apparatuses, fundus cameras and the like is performed by examiners using a manual switch. In the case where an examiner operates the apparatus with switches, however, if the examiner forgets to turn off the power supply after use, the life of electrical parts such as a lamp and the like is shortened and electric power is unnecessarily consumed. To overcome the above problems, some conventional apparatuses are provided with an auto-off function for automatically turning off the power supply if no operation is carried out for a prescribed time.

However, in the conventional apparatus loaded with the auto-off function, the power supplied to a microcomputer circuit etc. is not turned off even when operation is not performed, so that the unnecessary consumption of electric power can not be prevented sufficiently. The resulting drawback is the need for frequent battery charges or replacement of the battery apparatus of battery driving type.

To store sufficient electric power by one charge or change of battery in the battery type apparatus, the battery capacity thereof is required to be enlarged. As a result, the cost will increase and also the battery will be enlarged in size. This may be disadvantageous for apparatuses of hand-held type in particular.

The apparatus provided with the auto-off function has further a problem that return to an active condition from an auto-off condition needs a switching operation, and therefore, it is a cause of trouble.

SUMMARY OF THE INVENTION

The present invention has been made in view of the above circumstances and has an object to overcome the above problems and to provide an ophthalmic apparatus capable of working with simple operation and less consumption of electric power.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic apparatus of this invention comprises measuring means for measuring an eye of an examinee, detecting means for detecting whether the eye of the examinee is located within a predetermined area with respect to the apparatus, interval-time-signal-producing means for producing a prescribed interval time, power supply means for supplying power intermittently to the detecting means in accordance with the signals of the interval-time-signal-producing means, and means for generating a signal to initiate the supply of power required for driving the measuring means of the apparatus when said detecting means judges that the eye exists within the predetermined area.

Further, in the second aspect of the present invention, an ophthalmic apparatus comprises a measuring index projecting optical system for projecting cornea-shape measuring indexes onto an eye of an examinee and a measuring index detecting optical system for detecting corneal reflection images of the indexes projected on the eye by the measuring index projecting optical system, measuring light sources disposed in said measuring index projecting optical system, and detecting means disposed in the measuring index detecting optical system, and cornea-reflection image-detecting judging means for turning on the measuring light sources, and for judging whether corneal reflection images are detected by the measuring index detecting optical system, and means for activating the judging means repeatedly to turn on the measuring light sources in said measuring index projecting optical system to judge repeatedly whether corneal reflection images are detected by the detecting means and for turning off the measuring light sources each time the judging means detects no corneal reflection images, each activation of the judging means occurring after a prescribed lapse of time following an absence of detection of corneal reflection images.

According to the present invention, the apparatus is so constituted as to control automatically power supply and operation by detecting if an examinee's eye is located within a measurable range. Accordingly, the apparatus has the advantages that operation thereof can be simplified, an examiner may concentrate on observing and measuring the examinee's eye, and reduction of electric power can be attained.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of a preferred embodiment of an ophthalmic apparatus embodying the present invention will now be given referring to the accompanying drawings.

The ophthalmic apparatus in the present embodiment is a cornea-shape measurement apparatus of the hand-held type, which comprises generally a measurement unit internally provided with optical systems for measurement and observation and electric systems for control and calculation, a battery charger and a printer unit.

(Measuring unit)

FIG. 1(a) illustrates the front face, i.e., examiner's side, of a measurement unit 1 and FIG. 1(b) illustrates the or reverse face thereof.

As shown in FIG. 1(a), the measurement unit 1 comprises an observation window 2 which allows an examiner to observe an examinee's eye for alignment, a liquid crystal display 3 on which measurement results and other information are displayed, a clear switch 4 to clear measured values stored in a memory, a transmission starting switch 5 to transmit measured data to a printer unit, and switches 6 and 7 to designate the right or left eye of an examinee's eye examined. The lower part of the measurement unit 1 is grip-shaped so that the measurement unit 1 may be held in one hand of the examiner, and a battery 10 is stored removably in the lower part of the grip.

On the opposite face of the measurement unit 1 as shown in FIG. 1(b), numeral 11 identifies a contact for transmitting measured data to the printer unit on-line via a battery charger when the measurement unit 1 is set in the battery charger, numeral 12 identifies contacts for charging the battery 10. Numeral 13 identifies a light source for data transmission light which transmits the measured data to the printer unit using an optical signal, whereby data transmission can be achieved even when the measurement unit 1 is not set in the battery charger.

Figure 2:
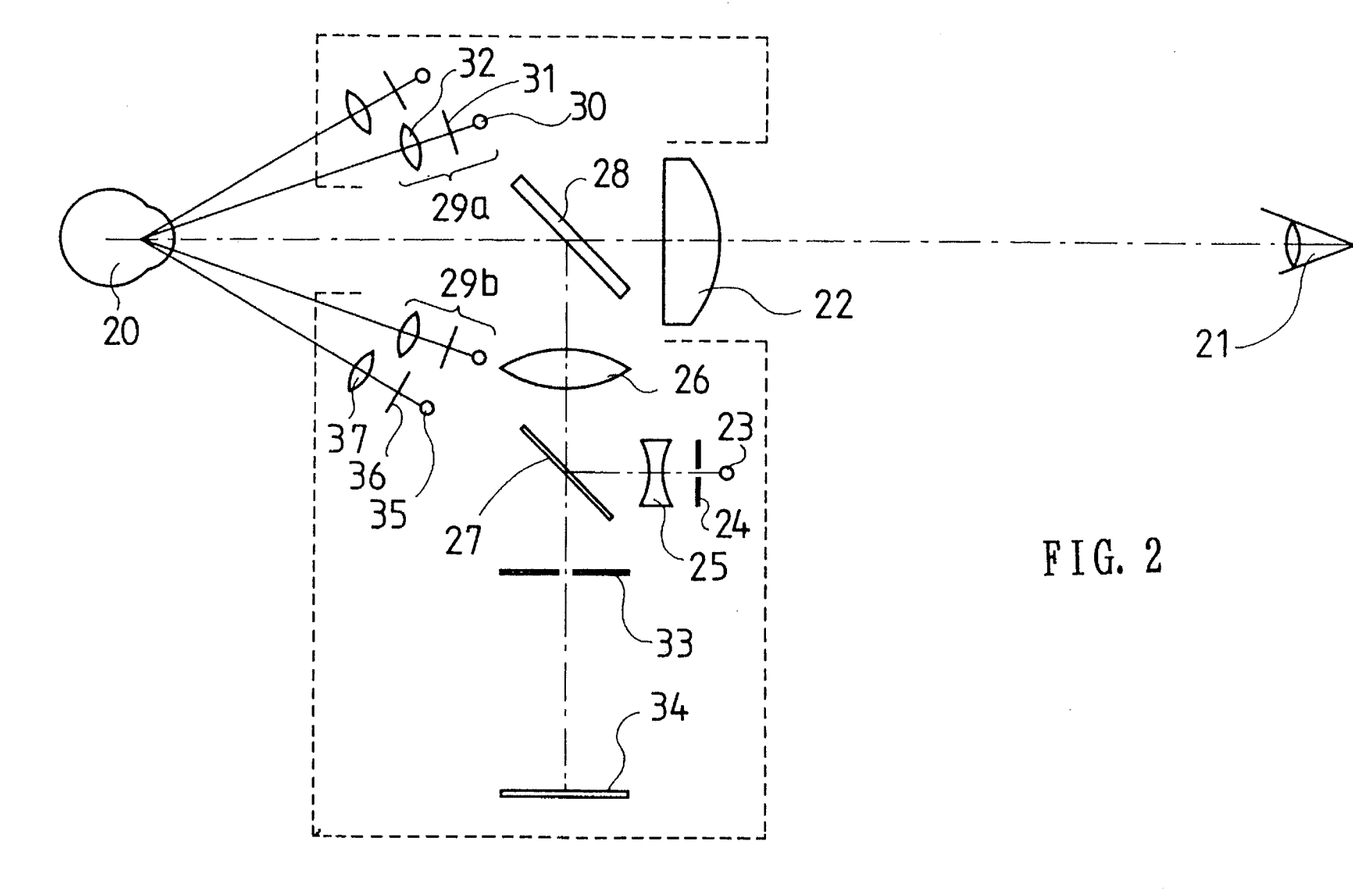
FIG. 2 is a schematic optical arrangement diagram of the ophthalmic apparatus in the first embodiment of the present invention.

FIG. 2 shows schematically an optical system of the measurement unit 1, which comprises a light source 23 of fixation index projecting light and a fixation index plate 24 having a spot aperture. Numeral 20 show an examinee's eye to be examined and numeral 21 shows an eye of an examiner who observes the examinee's eye 20 magnified through an observing lens 22.

Light emitted by the light source 23 illuminates the index plate 24 to project image thereof on the fundus of the eye 20 through a concave lens 25, a dichroic mirror 27, a focusing lens 26 and a beam splitter 28. Then, the examiner is allowed to view fixedly the index plate 24.

An index projecting optical system 29 which is to measure the shape of cornea comprises four optical sub-systems 29a–29d arranged apart from each other at a 90-degree angle in a circle about an optical path of observation light. Each of the sub-systems 29a–29d, wherein sub-systems 29c and 29d are not shown in FIG. 2, is constituted of a source 30 of measuring light such as a LED or the like which emits near-infrared light, a spot diaphragm 31 and a collimator lens 32. When detecting a working distance, the collimator lens 32 of the sub-system 29a will be removed out of the optical path of index projecting light of the sub-system 29a so as to form a finite index.

Numeral 33 identifies a telecentric diaphragm and disposed at a focal position of the focusing lens 26. Numeral 34 identifies a two-dimensional CCD sensor for detecting the position of corneal reflection images being formed by the index projecting optical system 29, which is disposed in a position that is in a substantially conjugate relationship with respect to about an iris on which corneal reflection images are to be formed through the focusing lens 26.

Numeral 35 are LEDs arranged apart from each other at a 30-degree angle in a circle about the optical path of observation light. Each of LEDs 35 is associated with a spot diaphragm 36 and a collimator lens 37. Corneal reflection images formed by the LEDs 35 in all will serve as mire-ring.

(Charger and Printer Unit)

Figure 3:
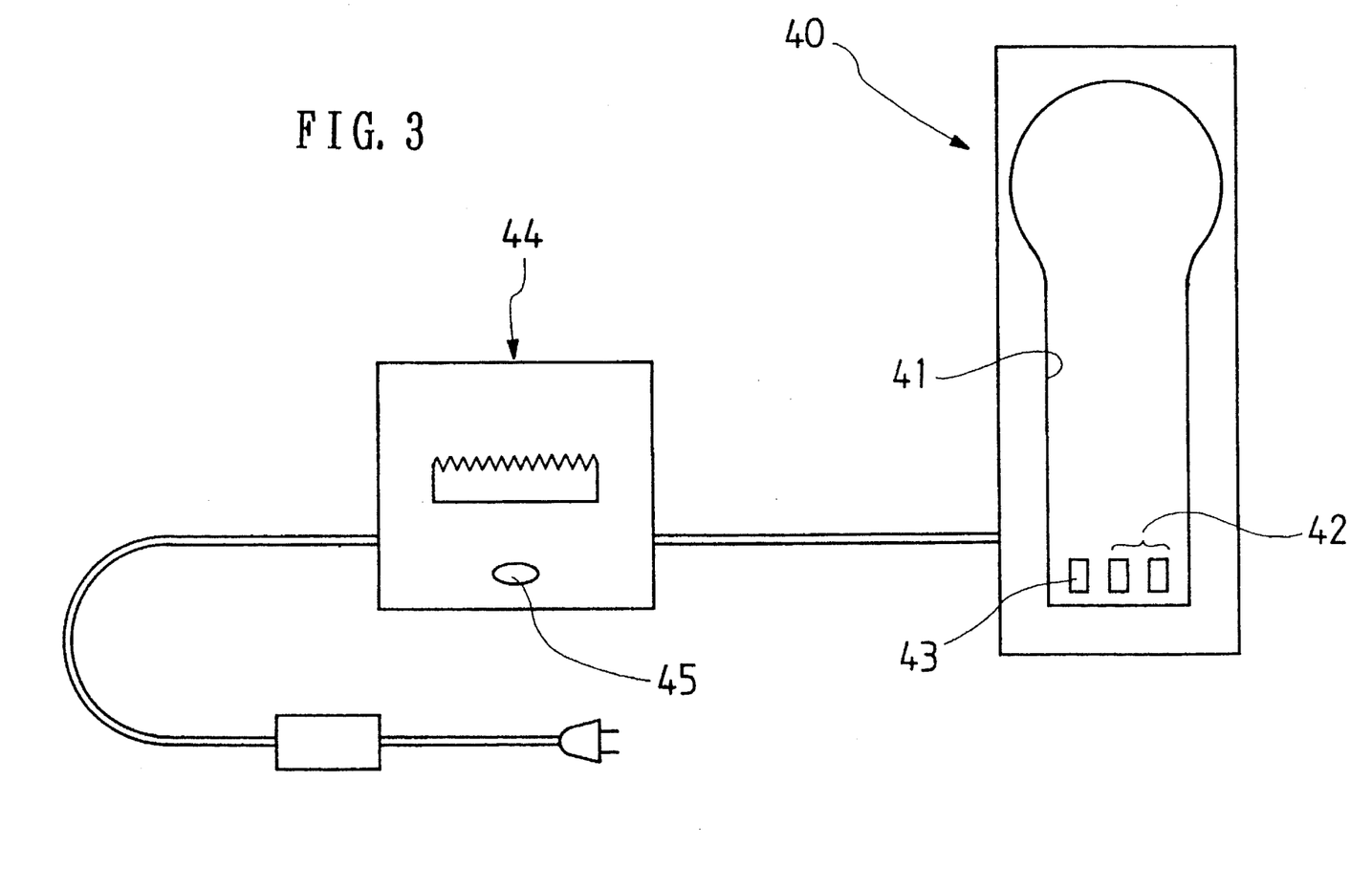
FIG. 3 is a schematic plan view of a battery charger and a printer unit of the ophthalmic apparatus in the first embodiment.

FIG. 3 shows a plan view of a charger 40 and a printer unit 44.

Charger 40 has a holder 41 in which the measurement unit 1 is to be set with the face shown in FIG. 1(b) downward, contacts 42 for battery charging and a contact 43 for data transmission. Simultaneously with being set in the holder 41, the measurement unit 1 is charged through the contacts 42.

Numeral 44 is a printer unit which is provided with a light receiving section 45 which receives optical signals during data transmission. The charger 40 and the printer unit 44 are connected with each other through a cable, and which are supplied with power source through an AC adaptor.

Figure 4:
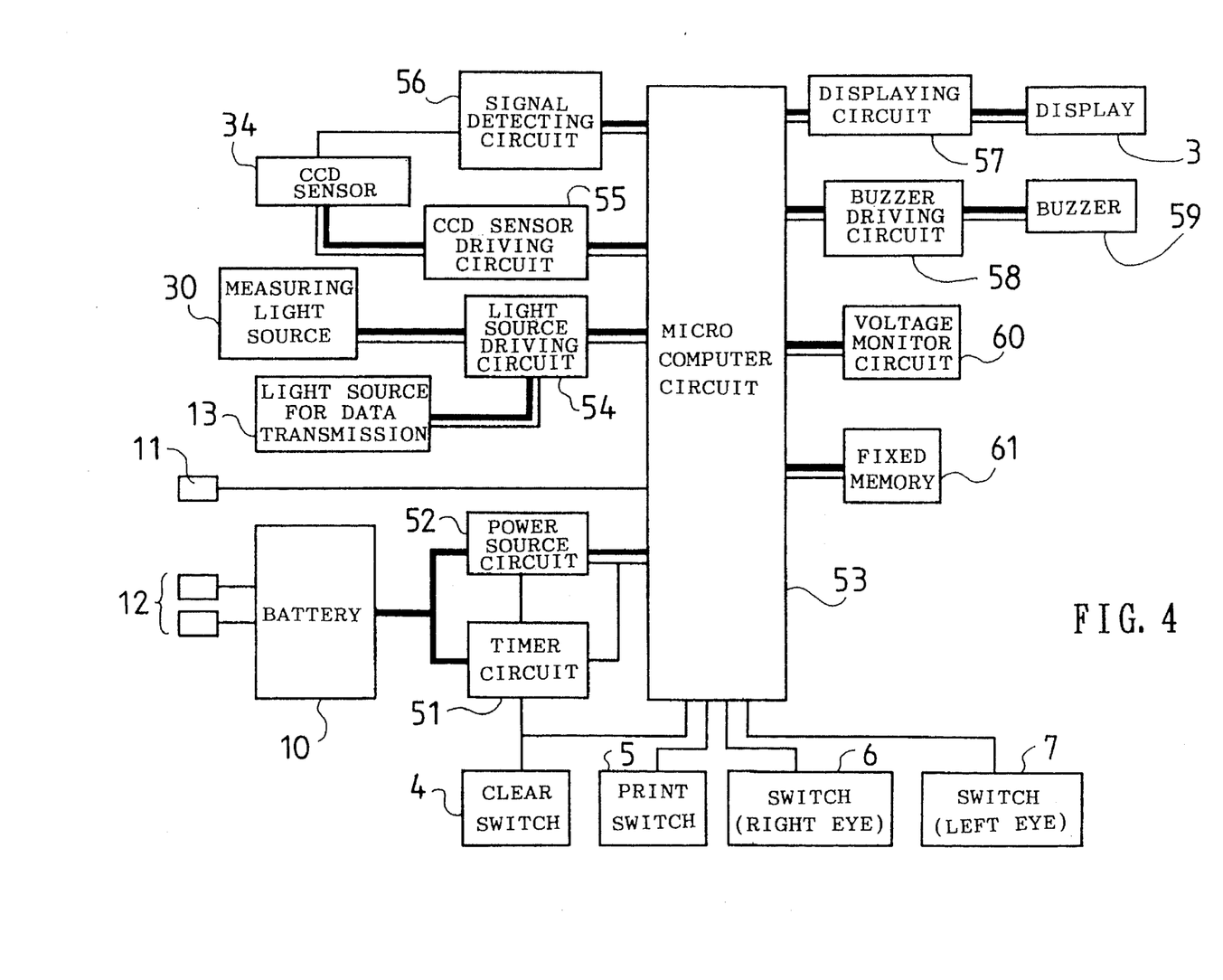
FIG. 4 is a circuit block diagram of the ophthalmic apparatus in the first embodiment.
Figure 5:
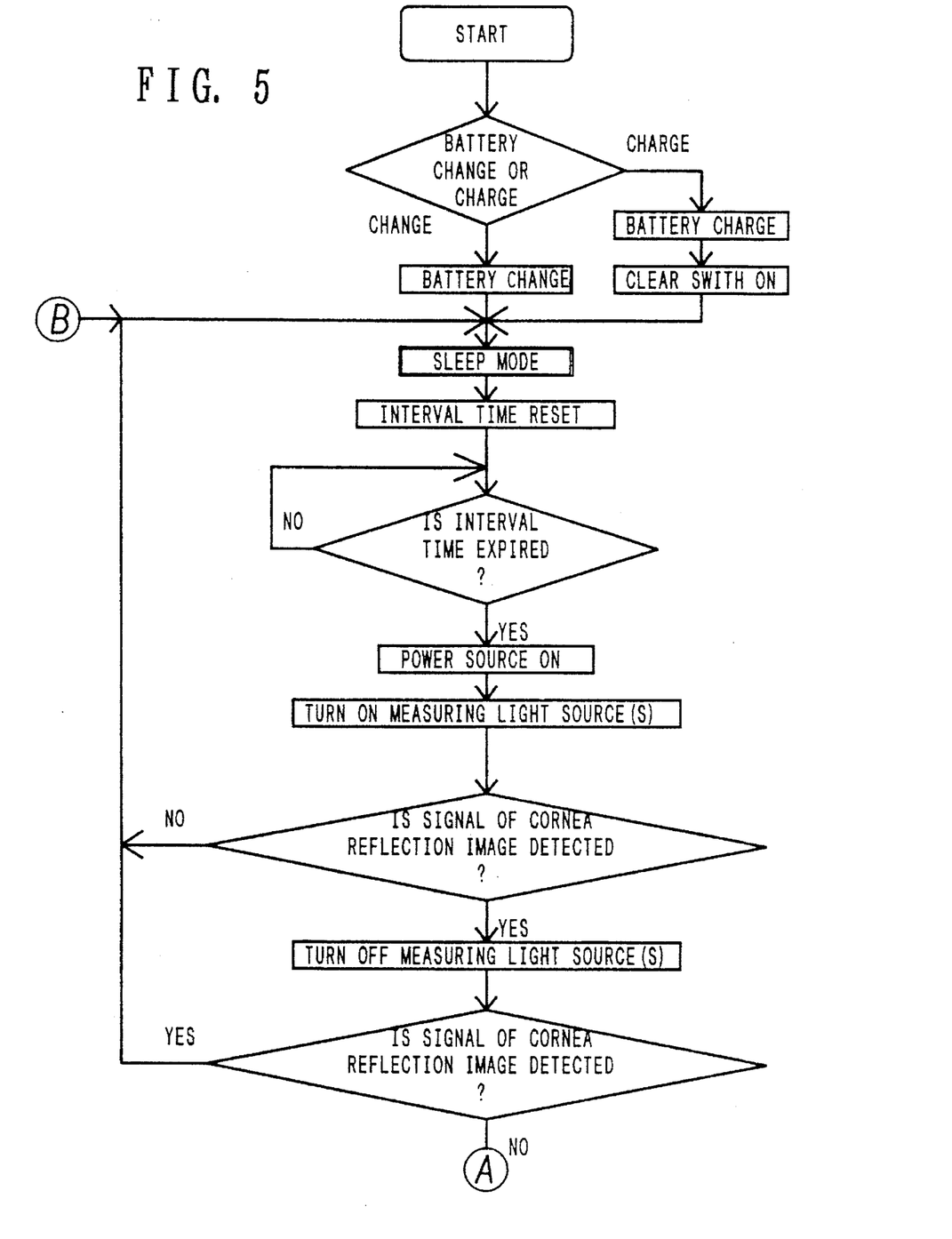
FIG. 5 is a flow chart for explaining the operation of the apparatus in the first embodiment.
Figure 6:
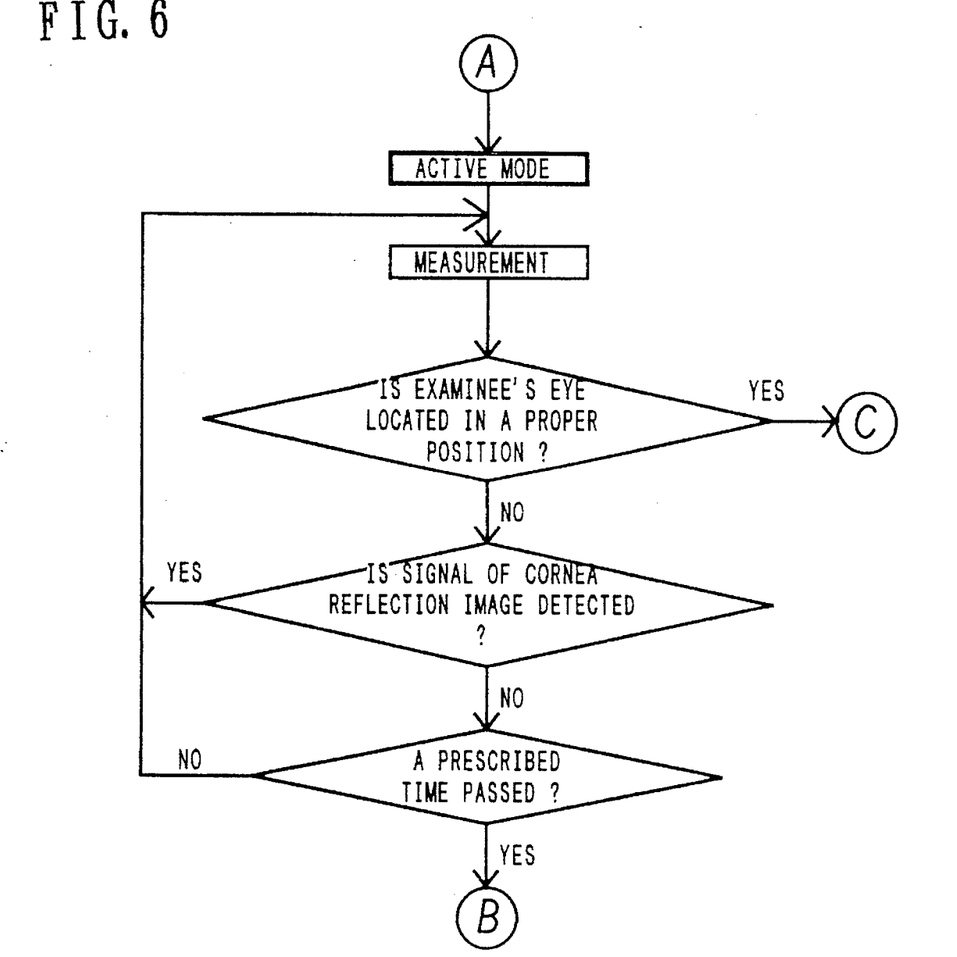
FIG. 6 is a flow chart for explaining the operation of the apparatus in the first embodiment.
Figure 7:
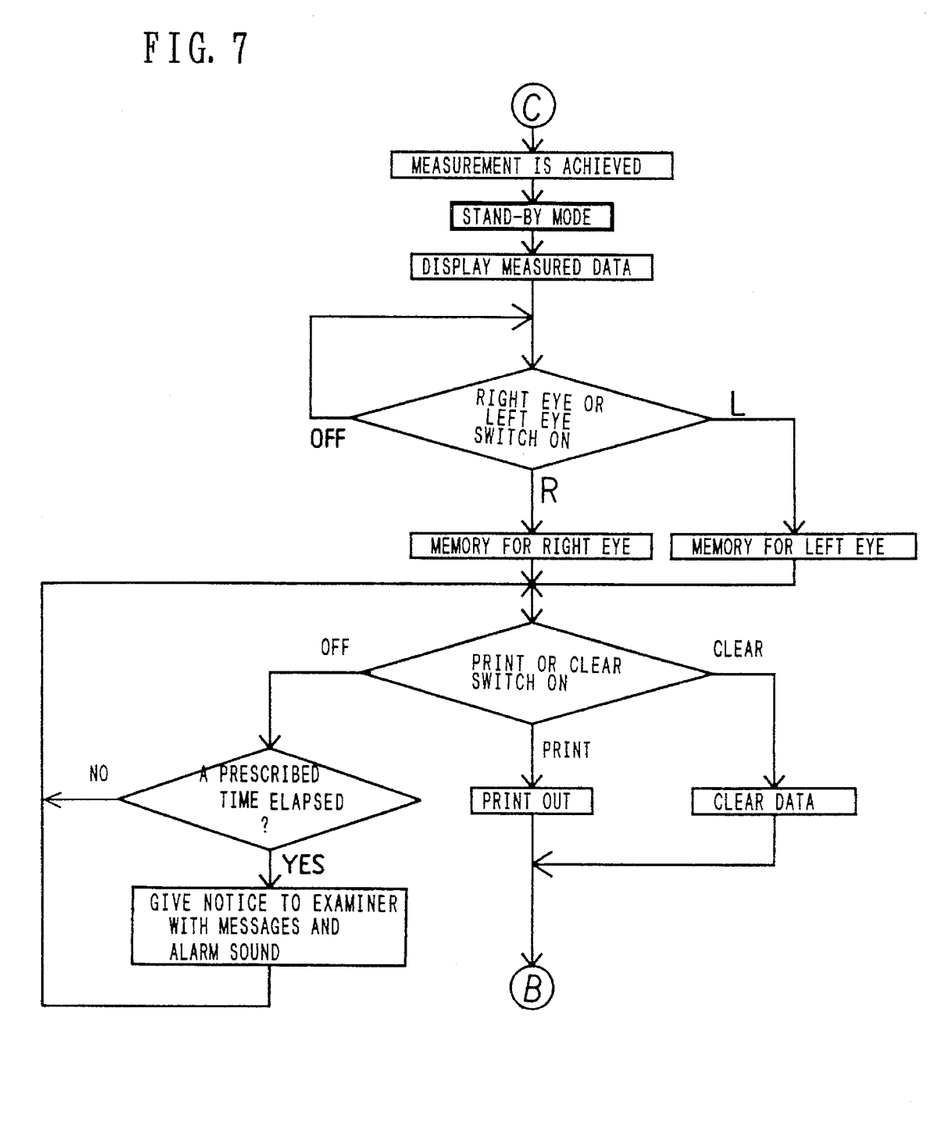
FIG. 7 is a flow chart for explaining the operation of the apparatus in the first embodiment.

Operation of the thus constructed apparatus will be explained referring to FIG. 4 showing a circuit block diaphragm and FIGS. 5–7 showing flow charts.

The measurement unit has three operational modes, namely, sleep mode, active mode and stand-by mode. Sleep mode is defined as a mode wherein power supply is cut off except for a timer circuit which produces interval time; active mode is defined as a mode wherein the corneal shape of an examinee's eye is measured successively; and stand-by mode is defined as a mode wherein, after measurement, measured data is memorized in a memory.

While receiving the power supply, microcomputer circuit 53 monitors battery voltage through voltage monitor 60. When the battery voltage becomes close to a prescribed voltage at which the circuit can not operate, the microcomputer circuit 53 displays message marks on a liquid crystal display 3 through a display circuit 57 to urge charge or change of battery and, at the same time, sounds a buzzer 59 through a buzzer circuit 58 to give notice to the examiner with an alarm.

When the battery voltage falls to an operational limit, the microcomputer circuit 53 writes the data in a fixed memory if measured data is being memorized in a memory, and then stops a timer circuit 51 and turns a power source circuit 52 off.

After charge or change of battery by the examiner, electric power is supplied to the timer circuit 51 and the measurement unit 1 is put in a sleep mode. When the timer circuit 51 starts to operate, the microcomputer circuit 53 checks the fixed memory 61 at the time of the initial check on an examinee's eye. If finding measured data therein, the microcomputer 53 will read in the data. After that, the mode is shifted to a stand-by mode and the data are displayed on the display 3.

When power is supplied to the battery 10, the measurement unit 1 is put in a sleep mode and then the power source is supplied to the timer circuit 51 to produce interval time. The timer circuit 51, after a predetermined time (for example, 2.5 seconds in the embodiment) has elapsed, transmits a start signal to the power source circuit 52. On receiving the signal, the power source circuit 52 is turned on to supply electric power to the microcomputer circuit 53. Then, the microcomputer circuit 53 drives a light source driving circuit 54 to turn on measuring light source 30 and, successively, drives a CCD sensor driving circuit 55 to operate a CCD sensor 34. The microcomputer circuit 53 checks through a signal detecting circuit 56 whether any signal, which is the corneal reflection image of the examinee's eye, is detected on the CCD sensor 34.

In a case where the signal detecting circuit 56 can not detect any signal of corneal reflection image, the microcomputer circuit 53 judges that the examinee's eye is not located within a measurable area and turns off the power source circuit 52, so that power supply is cut off except to the timer circuit 51.

The timer circuit 51 produces interval time. Then, the power source circuit 52 is turned on again after a predetermined time elapsed to similarly check whether the examinee's eye is detected within the measurable area.

In a case where the signal detecting circuit 56 detects optical signals, microcomputer circuit 53 turns off the measuring light source 30. The signal detecting circuit 56 judges that the examinee's eye is located within or close to the measurable area if any optical signal has not been detected. In a case where similar signal is detected though the measuring light source 30 is being turned off, microcomputer circuit 53 judges the optical signal detected is not caused by reflection of cornea of the examinee's eye but caused by external disturbance light and turns the power source circuit 52 off, so that the mode is shifted to a sleep mode. At the same time, the timer circuit 51 starts timer operation.

When judged that the examinee's eye is located within a measurable area, the microcomputer circuit 53 turns all the measuring light sources 30 on, the sleep mode being shifted to the active mode. The active mode can be achieved automatically, without needing manual operation by examiner, by only setting the measuring optical system of the measurement unit in a place where signal of images of the examinee's cornea can be obtained.

It is possible to turn on any number of measuring light sources 30 for checking the existence of an examinee's eye in accordance with the interval signal of the timer circuit 51. It is preferable to turn on one of measuring light sources 30 in behalf of the power saving effect and increasing the life of measuring light sources, and is more preferable to change the measuring light source to be turned on one by one every time.

When judged that the examinee's eye is located in a measurable area, the microcomputer circuit 53 turns all measuring light sources 30 on to measure the corneal shape of the examinee's eye. The examiner aligns the measuring optical system of the measurement unit with respect to the examinee's eye, so that signals of corneal reflection images come at a described proper location on the CCD sensor 34. Then, the microcomputer circuit 53 generates a trigger signal to start measurement of the shape of the cornea and processes in predetermined calculations to obtain measured data.

Explanations of alignment between the examinee's eye and the measuring system and calculations of the shape of cornea have been described in U.S. patent application Ser. No. 08/098,786 (Japanese Patent Application No. 4-224896) and Japanese Patent Publication No. 1-19896, both which were filed by the same applicant as the present invention. Therefore, detail explanations are omitted herein.

At the time of the active mode when the measuring light sources 30 all are being turned on, if a prescribed time (for example, 60 seconds in the embodiment) has elapsed or any signal of corneal reflection image come to be not detected on the CCD sensor 34, the microcomputer circuit 53 judges that the examiner stopped measurement and cuts the power source circuit 52 off to shift the active mode to the sleep mode.

When measurement on the examinee's eye is completed after alignment of the eye, the microcomputer circuit 53 shifts the active mode to the stand-by mode and drives the display circuit 57 to display the measured data on the display 3.

Figure 1:
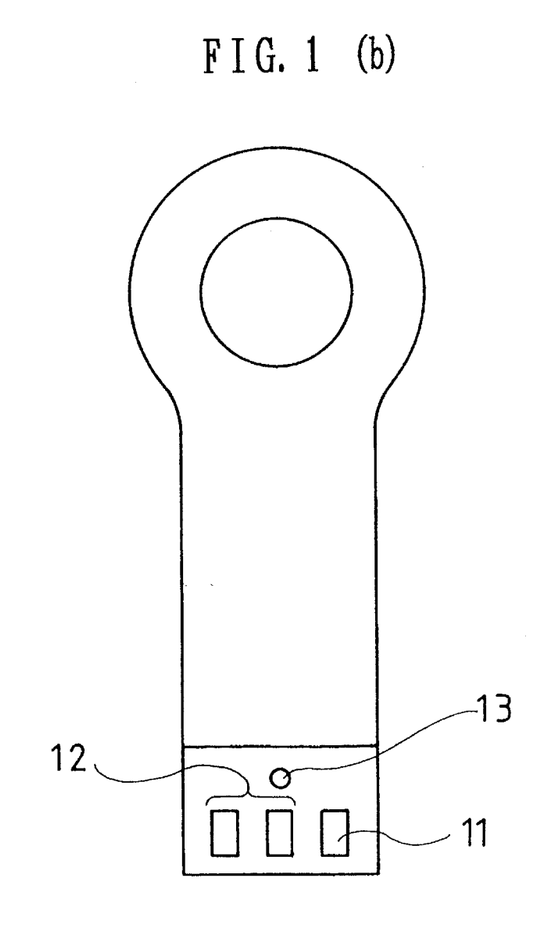
FIG. 1(a) is a schematic front view of a measurement unit of an ophthalmic apparatus according to the present invention, which show the side facing an examiner.
FIG. 1(b) is a schematic rear view of the measurement unit of FIG. 1(a)

Next, the examiner presses either switch 6 marked "R" in FIGS. 1 and 4 or switch 7 marked "L" to designate whether the measured eye is right or left. On receiving a signal from the switch 6 or 7, the microcomputer circuit 53 stores the designation of the measured eye with measured data of the eye in an internal memory.

If, in the stand-by mode where the measured data are being displayed on the display 3 after measurement, no switch operation has been performed for a prescribed time (for instance, 60 seconds), the microcomputer circuit 53 operates the display 3 to display a message to urge the next operation and also sounds the buzzer 59 through the buzzer driving circuit 58 to give notice to the examiner with an alarm.

The microcomputer circuit 53 succeedingly checks the existence of examinee's eye in accordance with an interval signal of the timer circuit 51, and the other eye of the examines will be measured in the same process as above.

After measurement, if requiring the measured data output, the examiner presses the print switch 5. When the print switch 5 is pressed, the microcomputer circuit 53 can transmit directly the measured data through the light source driving circuit 54 from the light source 13 for data transmission to the printer unit 44.

When the measurement unit is set in the charger 40, the microcomputer circuit 53 transmits the measured data through a contact 11 for data transmission and a contact 43 of the charger 40 to the printer unit 44. The printer unit 44 receives a communication signal through optical communication or a contact and prints out the measured data thereof.

On the other hand, if the measured data is unnecessary after measurement, the examiner presses the clear switch 4, so that the measured data stored in the internal memory of the microcomputer circuit 53 will be deleted.

When the print switch 5 or the clear switch 4 is pressed by the examiner, the power source circuit 52 is cut off and the stand-by mode is shifted to the sleep mode.

The present invention may be embodied in other specific forms without departing from the spirit or essential characteristics thereof. For instance, it is effective to apply the present invention particularly to hand-held type apparatuses by battery drive, but it is not limited thereto, the present invention may also be applied to conventional installed-type apparatuses.

In the above embodiment, though cornea reflection images formed by measurement light sources are utilized to check on the existence of an examinee's eye, another light source may be utilized and further different ways than optical detecting may be used.

Further, by additionally providing a function capable of changing the interval time and the shifting time from the stand-by mode to the sleep mode and the like in the apparatus of the embodiment, it is possible to obtain effective apparatuses according to use conditions.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and is in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:

measuring means for measuring an eye of an examinee;

detecting means for detecting whether the eye of the examinee is located within a predetermined area with respect to the apparatus;

interval-time-signal-producing means for producing a prescribed interval time;

power supply means for supplying power intermittently to said detecting means in accordance with said signals of said interval-time-signal-producing means; and means for generating a signal to initiate the supply of power required for driving said measuring means of the apparatus when said detecting means judges that the eye exists within the predetermined area.

2. An ophthalmic apparatus according to claim 1, wherein said detecting means comprises:

index projecting means for projecting detecting indexes onto the eye of the examinee;

optical detecting means for detecting reflection images of detecting indexes which are projected by said index projecting means; and judging means for judging existence of the eye based on results detected by said optical detecting means.

3. An ophthalmic apparatus according to claim 2, further comprising measuring index projecting means and measuring index detecting means, wherein said optical detecting means shares components with the measuring index detecting means.

4. An ophthalmic apparatus according to claim 1, wherein said apparatus is battery driven.

5. An ophthalmic apparatus according to claim 1, wherein said apparatus is a cornea-shape measurement apparatus.

6. An ophthalmic apparatus comprising a measuring index projecting optical system for projecting cornea-shape measuring indexes onto an eye of an examinee and a measuring index detecting optical system for detecting corneal reflection images of the indexes projected on the eye by the measuring index projecting optical system, the apparatus including:

measuring light sources disposed in said measuring index projecting optical system, land detecting means disposed in said measuring index detecting optical system, and cornea-reflection image-detecting judging means for turning on said measuring light sources, and for judging whether corneal reflection images are detected by said measuring index detecting optical system; and means for activating said judging means repeatedly to turn on the measured light sources in said measuring index projecting optical system to judge repeatedly whether corneal reflection images are detected by said detecting means and for turning off the measuring light sources each time said judging means detects no corneal reflection images, each activation of said judging means occurring after a prescribed lapse of time following an absence of detection of corneal reflection images.

7. An ophthalmic apparatus according to claim 6, further comprising means for shifting to an active mode of measuring the shape of a cornea of the examinee's eye when said cornea-reflection image-detecting judging means judges that the corneal reflection images are detected.

8. An ophthalmic apparatus according to claim 7, further comprising means for shifting to a sleep mode of supplying power only to a timer circuit in a case where said detecting means of said measuring index detecting optical system detects no signal of corneal reflection image for a prescribed time, when measuring the corneal shape of the cornea.

9. An ophthalmic apparatus according to claim 7, further comprising means for shifting to a stand-by mode for displaying measured data on display means at the time of completion of measurement measuring of measuring the shape of the cornea and for storing the measured data into memory means.

10. An ophthalmic apparatus according to claim 9, wherein the storing of measured data comprises switch means for storing respective measured data of the right and left eyes of the examinee in the memory means.

11. An ophthalmic apparatus comprising a measuring index projecting optical system for projecting cornea-shape measuring indexes onto an examinee's eye, a measuring index detecting optical system for detecting corneal reflection images of the indexes projected on the eye, a timer circuit for producing an interval time signal, a power source circuit which is turned on in accordance with an operation starting signal of the timer circuit and provides an on-signal, and a microcomputer circuit which is to be driven in accordance with the on-signal of the power source circuit to provide a drive signal, the apparatus including:

measuring light sources disposed in said measuring index projecting optical system in accordance with the drive signal from said microcomputer circuit, and detecting means disposed in said measuring index detecting optical system, and cornea-reflection image-detecting judging means for turning on said measuring light sources, and for judging whether corneal reflection images are detected by said measuring index detecting optical system; and means for activating said judging means repeatedly to turn on the power source circuit and the measuring light sources in said measuring index projecting optical system to judge repeatedly whether corneal reflection images are detected by said detecting means and for turning off the measuring light sources each time said judging means detects no corneal reflection images, each activation of said judging means occurring after a prescribed lapse of time following an absence of detection of corneal reflection images.

12. An ophthalmic apparatus according to claim 11, further comprising means for shifting to an active mode of measuring the shape of a cornea of the examinee's eye when said cornea-reflection image-detecting judging means judges that the corneal reflection images are detected.

13. An ophthalmic apparatus according to claim 12, further comprising means for shifting to a sleep mode of supplying power only to a timer circuit in a case where said detecting means of said measuring index detecting optical system detects no signal of corneal reflection image for a prescribed time, when measuring the corneal shape of the cornea.

14. An ophthalmic apparatus according to claim 12, further comprising means for shifting to a stand-by mode for displaying measured data on display means at the time of completion of measurement of the shape of the cornea and for storing the measured data into memory means.

15. An ophthalmic apparatus according to claim 14, wherein the means for storing measured data comprises switch means for storing respective measured data of the right and the left eyes of the examinee in the memory means.

\* \* \* \* \*

UNITED STATES PATENT AND TRADEMARK OFFICE
CERTIFICATE OF CORRECTION

PATENT NO. : 5,563,667
DATED : October 8, 1996
INVENTOR(S) : Naoki Isogai et al.

It is certified that error appears in the above-identified patent and that said Letters Patent is hereby corrected as shown below:

Title page, item [54] and col. 1, line 1,
<u>IN THE TITLE</u>:

Change the spelling of "OPTHALMIC" to --OPHTHALMIC--.

Claim 6, column 7, line 41, "land", should read --and--.

Claim 9, column 8, line 7, both occurrences of "measuring" should be deleted.

Signed and Sealed this

Fourteenth Day of January, 1997

*Attest:*

BRUCE LEHMAN

*Attesting Officer*  *Commissioner of Patents and Trademarks*